United States Patent
Strawder

[11] Patent Number: 6,017,149
[45] Date of Patent: Jan. 25, 2000

[54] APPARATUS FOR POSITIONING A PATIENT AND AN X-RAY CASSETTE NEXT TO EACH OTHER

[76] Inventor: Glenn G. Strawder, 8220 Northlake Ct., Laurel, Md. 20707

[21] Appl. No.: 09/094,680

[22] Filed: Jun. 15, 1998

Related U.S. Application Data

[63] Continuation-in-part of application No. 08/567,038, Dec. 4, 1995, Pat. No. 5,640,439, which is a continuation-in-part of application No. 08/265,111, Jun. 24, 1994, Pat. No. 5,973,664, which is a continuation-in-part of application No. 07/820,075, Jan. 13, 1992, Pat. No. 5,226,068.

[51] Int. Cl.[7] .................................................. G03B 42/02
[52] U.S. Cl. ........................................... 378/177; 378/180
[58] Field of Search ...................................... 378/177, 180

[56] References Cited

U.S. PATENT DOCUMENTS

| | | |
|---|---|---|
| 5,226,068 | 7/1993 | Strawder . |
| 5,473,664 | 12/1995 | Strawder . |
| 5,563,926 | 10/1996 | Brotzman ............................... 378/180 |
| 5,640,439 | 6/1997 | Strawder . |

Primary Examiner—Craig E. Church
Attorney, Agent, or Firm—William D. Hall

[57] ABSTRACT

An apparatus which attaches to the outer rim area or bottom surface area of an x-ray cassette holder used to support the x-ray cassette upright (parallel to or with the top surface of the holder) and next to the edge of a resting table or surface. The apparatus allows this particular type of cassette holder to rest the entire holder on top of a table and have the holder even, level or horizontal with the table top while the holder's slot supports the x-ray cassette upright perpendicular to the table top. The apparatus adjusts the holder into proper alignment so that the top of the slot and the top surface of the holder (including the outer edge or rim area) are even and horizontal to the top of the table.

7 Claims, 4 Drawing Sheets

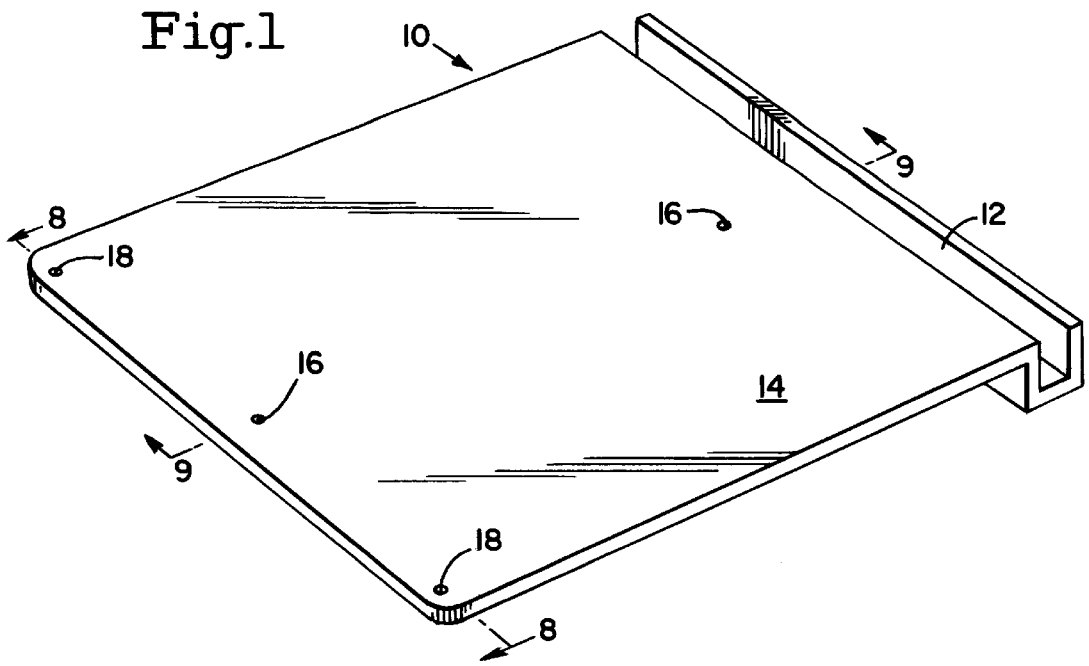
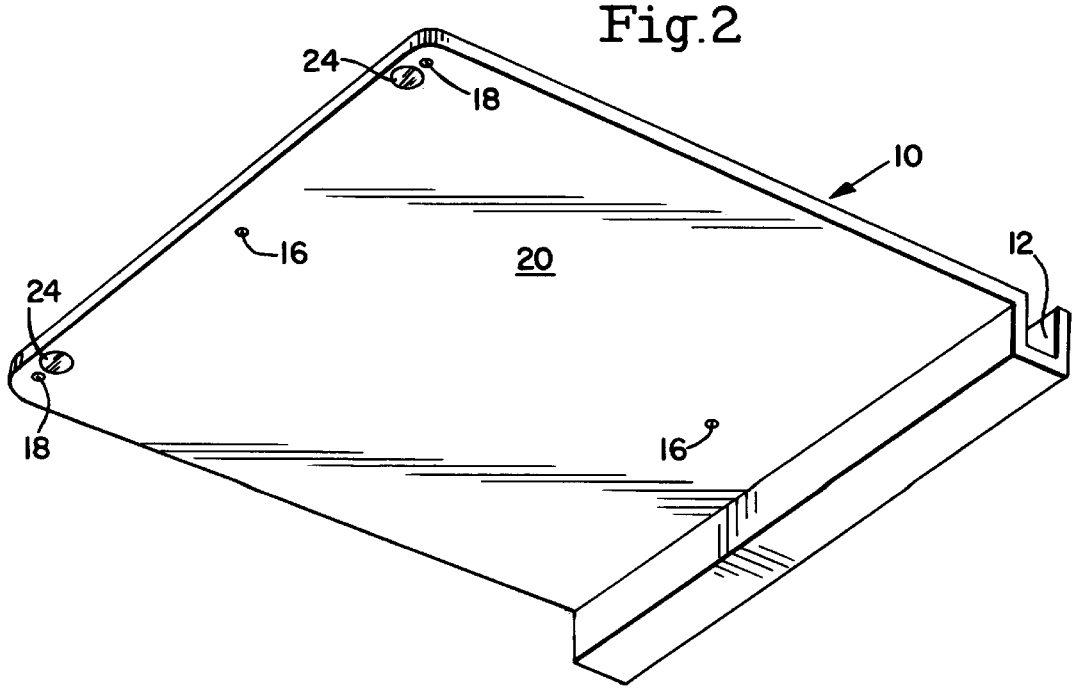

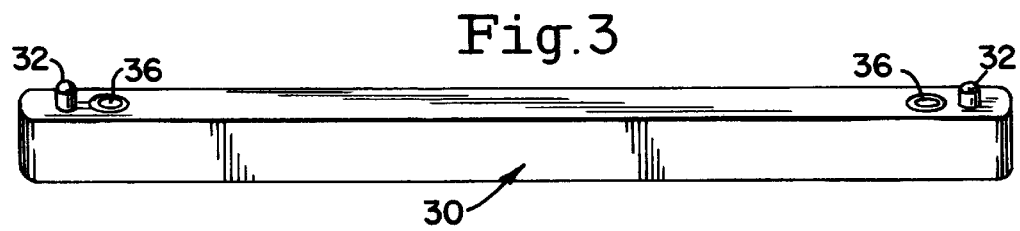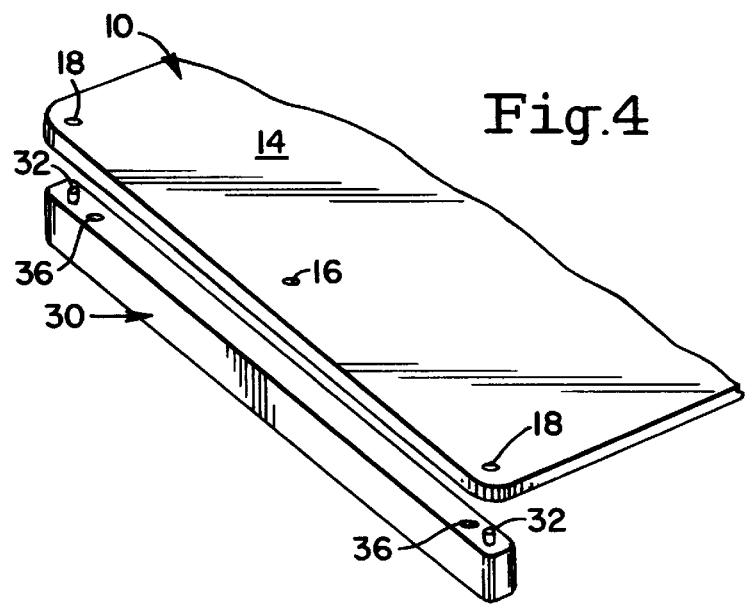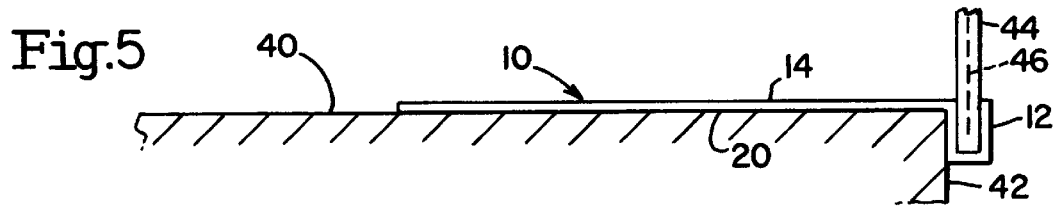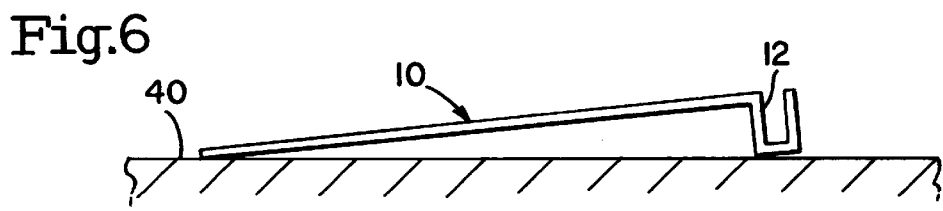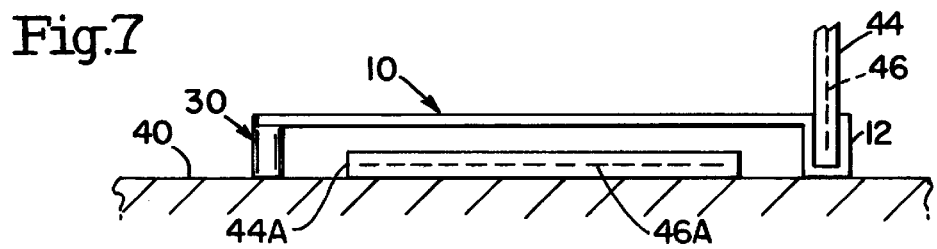

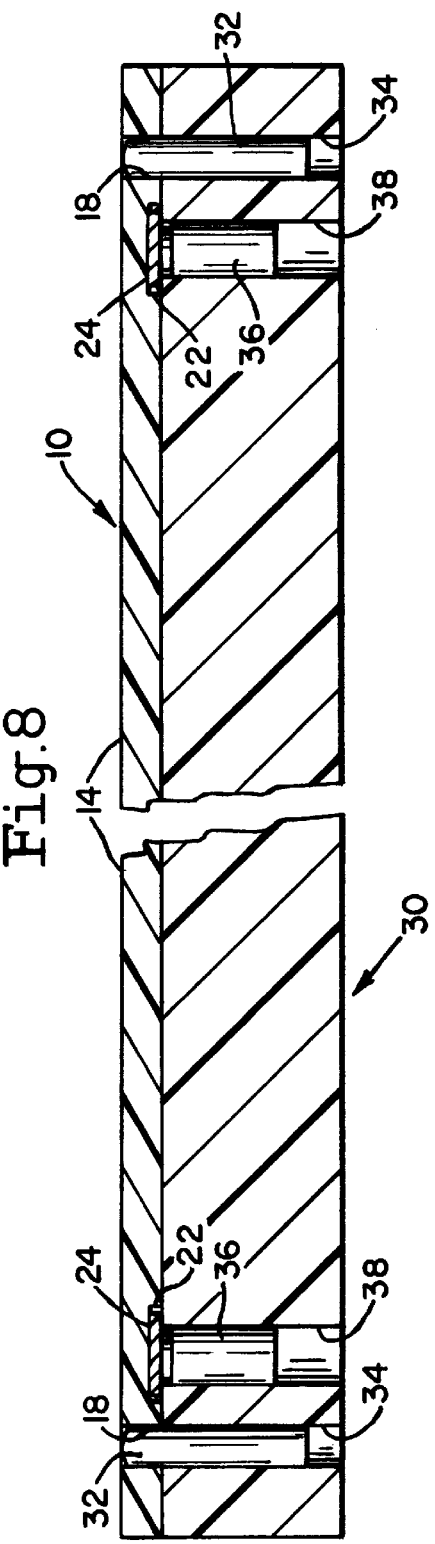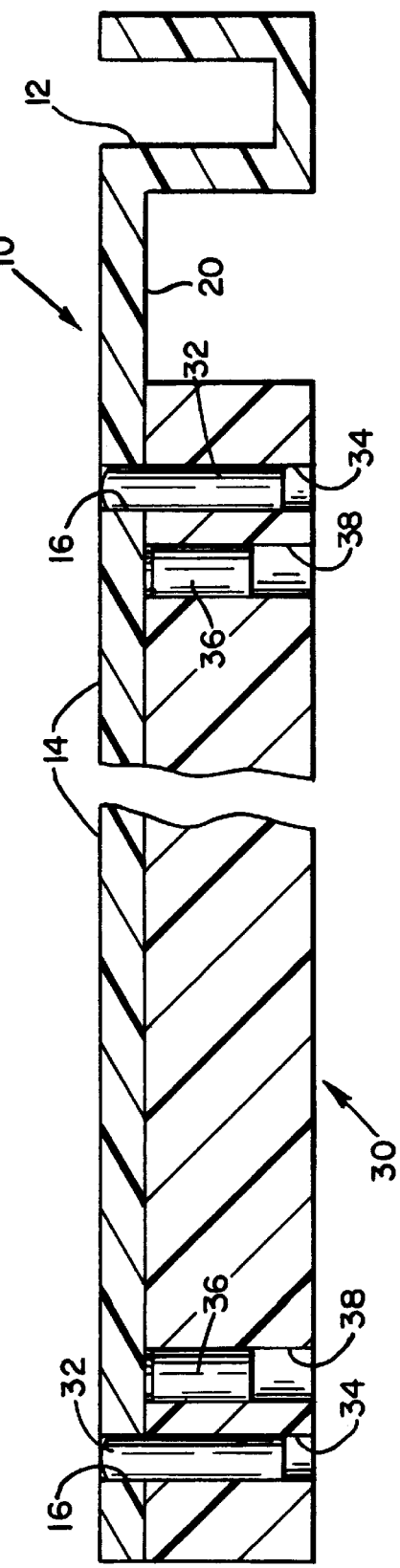

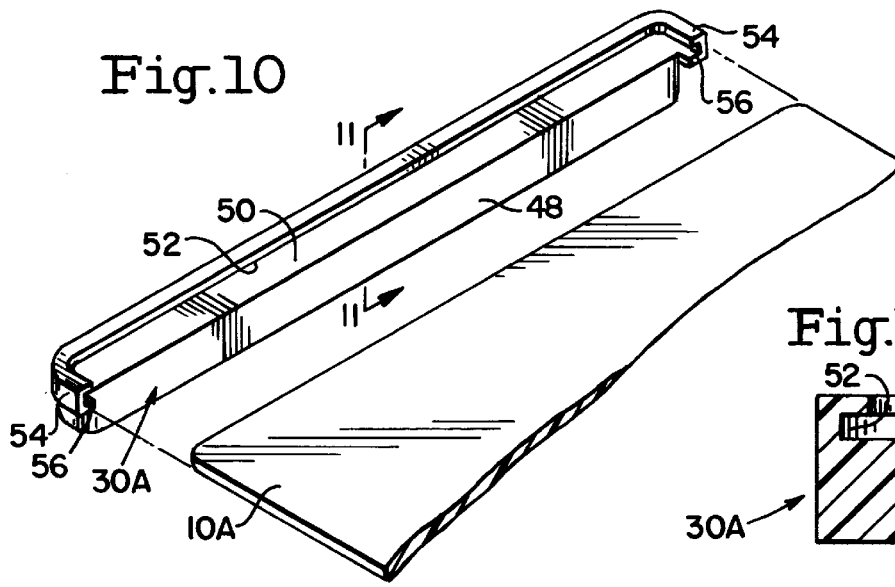
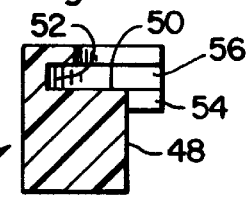
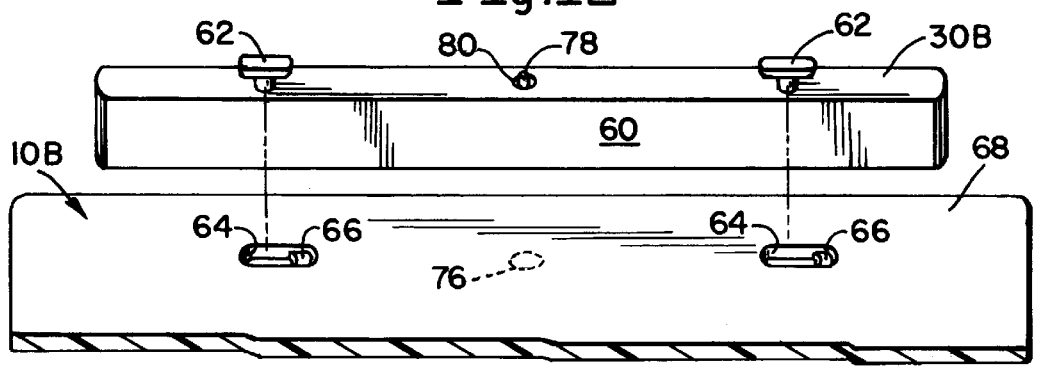
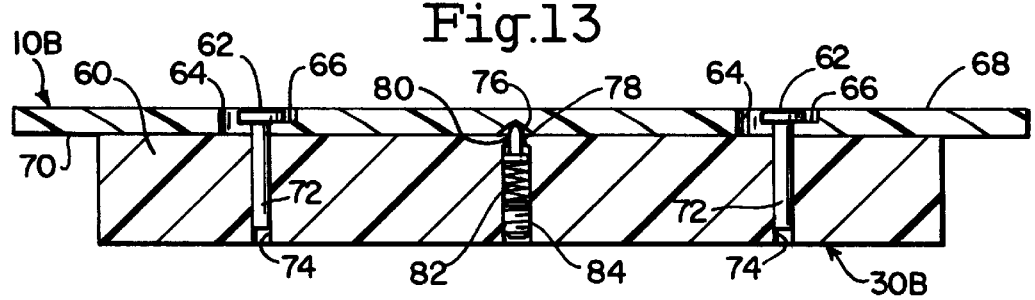

APPARATUS FOR POSITIONING A PATIENT AND AN X-RAY CASSETTE NEXT TO EACH OTHER

RELATED CASES

This application is a continuation-in-part of my prior application Ser. No. 08/567,038 filed Dec. 4, 1995, entitled Apparatus for Positioning a Patient for taking an x-ray, now U.S. Pat. No. 5,640,439, which application was in turn a continuation-in-part of my application Ser. No. 08/265,111 filed Jun. 24, 1994, entitled Method of and Apparatus for Positioning a Patient for the Taking of an X-ray, now U.S. Pat. No. 5,973,664, which application was in turn a continuation-in-part of my application Ser. No. 07/820,075 filed Jan. 13, 1992, now U.S. Pat. No. 5,226,068.

BACKGROUND OF THE INVENTION

This invention relates to an x-ray cassette holder used for holding an x-ray cassette upright on its edge while an x-ray of a body part of a human being or of an animal is being taken.

The prior art discloses means for positioning a patient adjacent to a cassette that holds an x-ray film. For example Strawder, U.S. Pat. No. 5,640,439 shows a type of cassette holder that can be place on the edge of a table top or a flat surface and support a cassette in the slot next to the edge. However, Strawder's holder would not be able to support an x-ray cassette level (perpendicular) to the top surface of the table if the entire cassette holder were lying on the top surface of the table.

SUMMARY OF THE INVENTION

The invention is an x-ray cassette holder that has the ability to hold an x-ray cassette upright either on top of a flat surface(table) and/or next to the side of the top of the flat surfaces edge. The present invention's cassette holder has a bottom surface area which is not totally level, flat or even across the entire bottom surface area as in FIG. 1. This shape is created so that the cassette holder can be used to hold an x-ray cassette upright and next to the edge or side of the top of the float resting surface area when the body part to be examined is also resting at or near the edge of the flat surface(table). This particular design cassette holder with an uneven bottom surface is useful in this kind of situation because during the taking of an actual cross-table lateral view the body portion the plate like area or body receiving part of the holder can easily slide underneath the body part being examined without the need to relocate the body part to the center of the table. The slot (which holds the x-ray cassette) is now located down along side and next to the edge or side of the top surface of the table where the body part is lying. The slot portion of this type of holder is used to receive and support the x-ray cassette and/or film and lower the film down below the body part being x-rayed so that the skin or downside anatomy of the body part in contact with the plate area or surface of the holder is not cut off the film for the x-ray. This particular type of x-ray holder is generally not used to perform any type of cross-table lateral view(side view) when the operator needs to place the entire bottom surface of the holder on top of the resting surface or table. However, the present invention makes it possible for this shape or design holder to be useful while lying entirely on top of a table. The invention's support bar is capable of supporting the outer rim area and/or underneath surface of the cassette holder. The support bar may comprise many different methods to engage with either the top surface, the border or rim area of the holder and/or the undersurface of the plate or body portion of this particular holder. The support bar is attachable and/or detachable to the x-ray cassette holder to support and maintain that portion of the holder in a level or even plane manner when the entire cassette holder is needed to rest on top of some type of table/bed (surface) during the taking of an x-ray. The support bar is employed to lifting up and supporting in a level (zero degree or horizontal plane) plane or position the opposite end of the holder than the portion or end of the holder with the slot that receives and supports the x-ray cassette/film upright. Once the support bar is employed an x-ray cassette can now be place underneath the plate or body portion of the holder (see FIG. 7). This particular location for the x-ray cassette will help produce the AP or frontal view of the body part being x-rayed. While with the body part in the same position be now changing the location of the x-ray cassette to the slot of the holder will produce a Lateral or side view of the same body part being resting on the plate area of the holder. Also, since the slot portion of the holder is lower then the plate portion of the holder support is needed to lift up and level the plate area of the holder which generally slopes downward and touches the flat resting surface when the holder of this particular shape(form) is resting entirely on top of a flat resting surface without a support bar present. The slot portion of this type of holder is used to receive and support the x-ray cassette and/or film and lower the film down below the body part being x-rayed so that the skin or downside anatomy of the body part in contact with the surface of the holder is not cut off the film for the x-ray. This type of x-ray holder is generally not used to perform any type of cross-table lateral view (side view) when the operator needs to place the entire bottom surface of the holder on top of the resting surface of the body part unless it employs the support bar.

The present invention's cassette holder is even or level when the entire cassette holder is placed on top of a flat surface and the support bar is employed. The support bar or bridge bar of the present invention is capable of being attachable (mounted) to the rim, sides and/or undersurface (bottom) of the holder. This bar or bridge when in place will assist in leveling out and supporting the uneven portion of the holder evenly and upright with the remainder of the holder resting on top of a table. This same portion of the holder being supported now being supported in a level manner is also the portion of the holder which is used to locate and support the body part being x-rayed. The invention is detachable from the rim and/or under surface of the cassette holder allowing the holder to be used on the edge of a table when detached and on the top of a table when attached. However, the invention is not limited to the methods described in this application for attaching and detaching the invention to this type of x-ray cassette holder. The present invention may be electronically and/or mechanically attached, detached and operated.

Without the support bar present this particularly designed or shaped x-ray cassette holder of the present invention is useful for table-edge cross-table lateral work or views such as lateral Cervical, Thoracic as well as Lumbar spines, etc. however, with the support bar in place this particularly designed cassette holder is transformed into a holder capable of being useful in doing table-top cross-table lateral work or views such as lateral knee, ankle, etc.

To attach or detach the support bar from a holder the user may simply in one hand holds the holder so that the outer rim area and/or bottom surface is seen. Then in the other hand holds the support bar with the pins on the bar facing outward and toward the holes (if any) in the holder. The operator brings the bar and holder closer together by placing the pins of the bar thru the bottom side holes or opens in the holder's surface. The operator then with a small amount of force presses the bar against the surfaces of the holder and in the case of FIG. 12 and FIG. 13 slides the bar less then a half an inch in the only direction it will move in. When the bar stops sliding it is secure in position and will not fall off the holder. To removed the bar the operator simply does the opposite of the two steps described above used to locate the bar to the holder. Whether locating or removing the bar the two steps are generally performed in 3–5 seconds.

In general, the present inventions or cassette holder is capable of holding and x-ray cassette upright on its end either on top of a table and/or next to the edge of the table. Without the invention's support bar present the invention's plate like or body part receiving area bottom surface will rest on the table's top while the slot for supporting the cassette will be located next to the same table's edge. With the support bar in place the invention's plate like or body part receiving area is elevated upwards away from the top surface of the table. The entire cassette holder can now rest evenly on top of the table. The bottom surface of the plate like portion of the holder is no longer in contact with the top surface of the table. There is now a tunnel or open area between the support bar and the slot portion of the holder. This tunnel or opening allows the user to place an x-ray cassette in the opening to allow more then one plane or view of the body part rest on the receiving area to be taken.

BRIEF DESCRIPTION OF THE DRAWINGS

FIG. 1 is a top perspective view of the invention.

FIG. 2 is a bottom perspective view thereof.

FIG. 3 is an oblique view of a support bar.

FIG. 4 is a fragmentary perspective view a holder outer end portion with a support bar below it ready for assembly.

FIG. 5 is a diagram of a holder used on the edge of a patient support table in proper position.

FIG. 6 is a diagram of the same type of holder as in FIG. 5, when it is used improperly to rest entirely on top of a patient support table.

FIG. 7 is a diagram of the same type of holder as in FIG. 5 and 6, with support bar in place.

FIG. 8 is a cross-section taken along lines 8—8 of FIG. 1, but with a latitudinally mounted support bar attached.

FIG. 9 is a cross-section taken along lines 9—9 of FIG. 1 with a longitudinally mounted support bar attached.

FIG. 10 is a top perspective view of another type of support bar with a fragmentary end of a holder spaced in close proximity.

FIG. 11 is a cross-section taken along lines 11—11 of FIG. 10 thru the type of support bar.

FIG. 12 is a top perspective view of still another type of support bar and the end portion of a holder spaced closely thereto.

FIG. 13 is a cross-section similar of FIG. 12 showing the holder and the support bar attached.

BRIEF DESCRIPTION OF THE DRAWINGS

FIG. 1 a cross table lateral x-ray cassette holder 10 used to hold x-ray cassettes and films upright in slot 12 with the x-ray film and slot 12 resting next to or adjacent to the edge of table top surface 40. The holder's top surface 14 is used to locate a body part near slot 12.

FIG. 2 shows the bottom surface 20 of holder 10. The longitudinal holes 16 and the latitudinal holes 18 located in holder 10 allow the pins 32 of the support bar 30 in FIG. 3 to be attached to the underside of holder 10 an support either the outer end or rim of holder 10 and/or the middle of holder 10 bottom surface 20 in an even or horizontal plane with the top surface of table 40. The longitudinal holes 16 allow the support bar 30 to be able to hold upright the outer end or rim area of holder 10 in an even or horizontal plane with the top surface of table 40. The longitudinal holes 16 allow the support bar 30 to be able to hold upright the outer end or rim area of holder 10 so that an x-ray cassette and/or film can be placed underneath the body support portion of holder 10 where a space would normally be when the support bar 30 is in place (see FIG. 7. The latitudinal holes 18 allow the support bar 30 to be able to hold upright holder 10 even if a portion of the outer end or rim area of holder 10 is hanging over the edge of a flat surface or table top 40, holder 10 is held in an even or horizontal plane with the top surface of table 40. Support bar 30 may also be attached to holder 10 a any diagonal fashion to slot 12 (not illustrated). Magnets 36 next to the pins 32 may align with contact buttons 24 when pins 32 are in place to keep the support bar 30 form falling away from holder 10 when bumped or held in the air or carried.

FIG. 5 shows the typical or correct way cross table lateral x-ray cassette holder 10 holding upright in slot 12 a cassette 44 with an x-ray film 46 inside and perpendicular with (the body part and x-ray beam not shown) the top surface 16 of holder 10 while the bottom surface 20 of holder 10 is in contact with table top surface 40 and the inside side surface of slot 12 is in contact with the table's edge 42. The top surface 14 of holder 10 is parallel with the table top surface 40 and perpendicular with slot 12 and cassette 44.

FIG. 6 shows the entire cross table lateral x-ray cassette holder 10 resting on table top surface 40 and how uneven, angled or off the horizontal or perpendicular plane an x-ray cassette will be in slot 12 when the entire holder 10 is place on table top surface 40 and the edge or rim of the holder 10 is resting on table top surface 40 and at the same time slot 12 is angled downward toward top surface of table 40. The top surface 14 of holder 10 is also at an angle. This means that if a grid type cassette 44 was in slot 12 the gird type cassette 44 would also be angled downward toward to top surface of table 40 and not perpendicular with the top surface of table 40. In the field of Radiology (especially when the type of cassette being used is a grid) it is important to align the x-ray beam parallel to or with x-ray cassette 44 and film 46 to produce a good image quality of the body part being x-rayed. When using a gird is proper alignment is not done a significant amount of image quality will be lost do to the lead stripe inside the grid absorbing more of the radiation then wanted or required.

FIG. 7 shows what happens to the holder 10 as described in FIG. 6 when the support bar 30 of the invention is connect or attached to the outer rim and/or bottom surface 20 of holder 10. The top surface 14 of holder 10 is now parallel with table 40 and slot 12 is now level when holding cassette 44 and film 46 upright. Cassette 44 and slot 12 are now perpendicular to or with the top surface 14 of holder 10 and table 40. Although now body part or x-ray beam is drawn in FIG. 7, if an x-ray beam and body part were present the body part would be resting on the support bar 30 while the x-ray beam would be to the (as you look at FIG. 7 the support bar 30 is located to the left of the illustration.) left of the end of the holder 10 with the support bar 30. The x-ray beam would be directed to intersect with the body part an then the x-ray cassette 44 and film 46. In this positioning the x-ray beam is considered to be perpendicular to x-ray cassette 44 and film 46. Also, when a grid type of x-ray cassette 44 is employed, it must be held straight upright as in FIG. 5 and FIG. 7 to produce a satisfactory image of the body part being x-rayed. FIG. 7 also shows how an x-ray cassette 44A would fit under the bottom surface 20 of holder 10. The x-ray cassette 44A is between support bar 30 and slot 12.

FIG. 8 show a cross-section of holder 10 with the support bar 30 connected in a latitudinal manner. FIG. 9 shows a cross-section of holder 10 with support bar connected in a longitudinal manner. It must be understood that the support bar 30 may be at any location along the rim of holder 10 and at any angle or position on bottom surface 20 of holder 10.

FIG. 10 shows a modified form of the invention in which support bar 30A can be attached to the outer rim area of holder 10A. This is done by sliding the outer edge or rim of holder 10A into slot 52. FIG. 11 is a cross-section of the support bar 30A shown in FIG. 10.

FIG. 12 is still another, modified form of a method to connect support bar 60 to holder 10B. T-shape pin tops 62 of support bar 30B fit in holes 64 of holder, then slide slightly to a resting point so that one side of the T-shape pin 62 will rest on top of slot shelf 66. FIG. 13 shows instead of using magnets 36 to give added support as in FIGS. 8 and 9 a pin 78 is employed and located on support bar 30B that protrudes slightly upward and away from the top surface of support bar 30B. The pin 78 fits in dent 76 located on the bottom surface 70 when the support bar 30B and holder 10B make contact to give more support to the connection. Pin 76 may be connected to a spring 82 to give it a little resistance when located in detent 76 of holder 10B.

I claim:

1. A device for positioning a part of a patient adjacent an X-ray cassette for the purpose of taking an X-ray, comprising:

means for positioning a patient adjacent an X-ray cassette comprising a plate and a socket, said plate comprising means for receiving a part of a patient to be X-rayed, said plate defining at least one wall of an elongated cavity that forms said socket and has sufficient width to receive an X-ray cassette, said plate having an end, said cavity being adjacent said end, said plate having an area for receiving the part, of the patient, to be X-rayed, said cavity being located between said area and said end, said plate having an upper surface for receiving said part of a patient and an under surface, said socket having a portion extending further downwardly than said under surface, and support means for supporting said plate at a location spaced from said end.

2. A device as defined in claim 1 in which said support means has a thickness about equal to the amount that the socket extends further downwardly than said under surface so that said plate will be substantially level when the device is placed on a horizontal surface.

3. A device as defined in claim 2 in which said support means has sufficient thickness to permit an X-ray cassette to be placed on said surface and under said plate.

4. A device as defined in claim 1 in which said socket comprises means for holding an X-ray cassette upright.

5. A device as defined in claim 2 in which said support means is elongated.

6. A device as defined in claim 2 in which said support means and said plate have mating means for temporarily connecting said support means and said plate together.

7. A device as defined in claim 6 in which said socket is elongated and in which said support means in elongated and said mating means permits said support means to be attached to said plate with different orientations relative to said socket.

* * * * *